United States Patent [19]
McWhirter et al.

[11] Patent Number: 4,878,180
[45] Date of Patent: Oct. 31, 1989

[54] METHOD OF EVALUATING THE CONDITION OF TUBULAR GOODS

[75] Inventors: Vernie C. McWhirter, Pearland; James E. Pickett; Norman R. Carlson, both of Houston, all of Tex.

[73] Assignee: Western Atlas International, Inc., Houston, Tex.

[21] Appl. No.: 799,226

[22] Filed: Nov. 18, 1985

[51] Int. Cl.⁴ .................. G01N 29/04; G06F 15/20
[52] U.S. Cl. ............................ 364/507; 73/592; 324/220; 324/228
[58] Field of Search ............... 364/507, 512, 551; 324/219–221, 216, 228; 73/592, 598, 600, 614–616, 622, 623

[56] References Cited

U.S. PATENT DOCUMENTS

| 3,543,144 | 11/1970 | Walters et al. | 324/221 |
| 4,274,288 | 6/1981 | Tittmann et al. | 364/507 |
| 4,522,064 | 6/1985 | McMillan | 73/592 |
| 4,571,999 | 2/1986 | Arita et al. | 73/598 |
| 4,628,260 | 12/1986 | Kimoto et al. | 324/220 |
| 4,628,261 | 12/1986 | Hüschelrath et al. | 364/507 |
| 4,663,727 | 5/1987 | Saporito et al. | 73/623 |

OTHER PUBLICATIONS

"Dresser Atlas Casing Evaluation Services", The Vertilog Survey, Aug. 1985, pp. 17–40.

Primary Examiner—P. S. Lall
Assistant Examiner—Brian M. Mattson
Attorney, Agent, or Firm—Patrick H. McCollum

[57] ABSTRACT

A method for evaluating the extent of deterioration of pipes whereby an inspection instrument is passed through a length of casing to determine the extent of corrosive deterioration. The resulting measurements generated by the inspection instrument are processed to exclude those responses caused by the structural configuration of the casing length under inspection. The remaining responses are then analyzed to compile a detailed interpretation of the measurements including specific information regarding the state of deterioration of the length of casing under inspection.

8 Claims, 3 Drawing Sheets

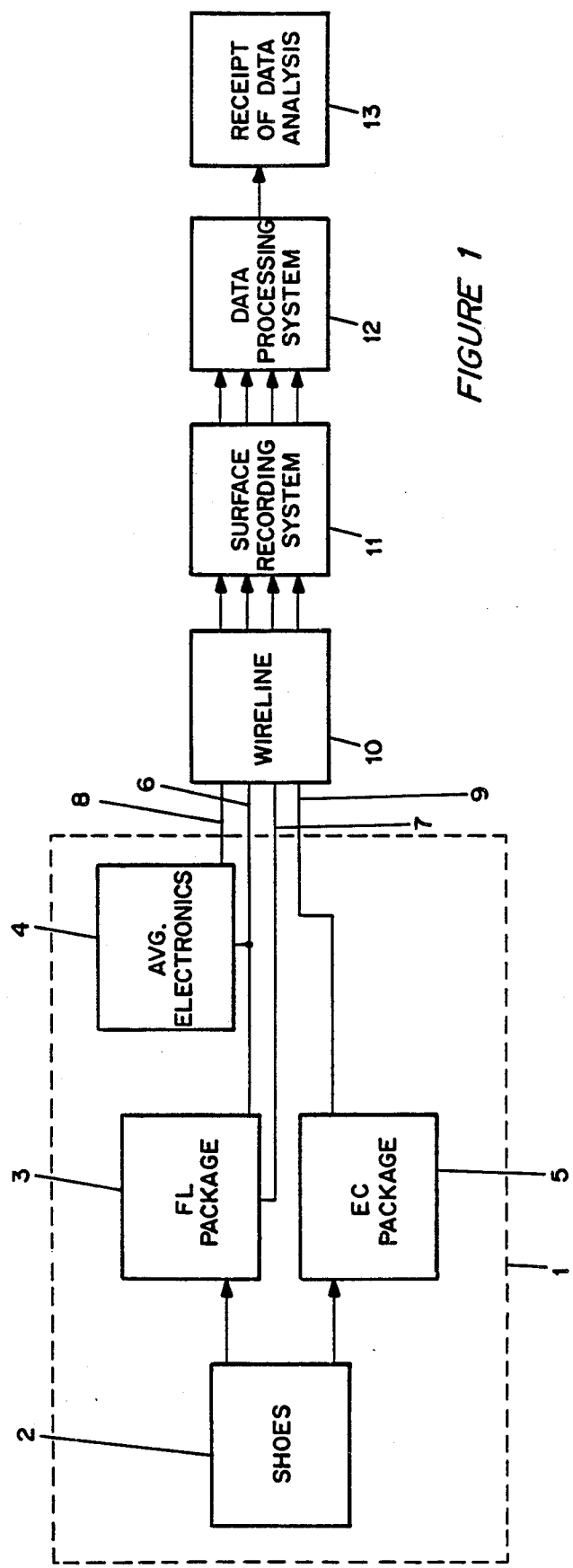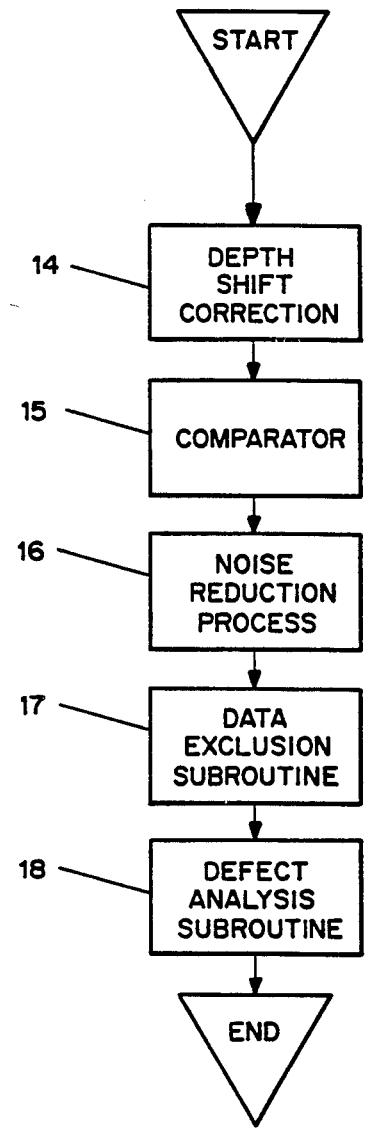

METHOD OF EVALUATING THE CONDITION OF TUBULAR GOODS

BACKGROUND OF THE INVENTION

This invention relates to methods and apparatus for evaluating the condition of oilfield tubular goods and the state of deterioration of subsurface pipe or casing.

A variety of problems may result from the deterioration of subsurface casing. Drill pipe collars may rub the casing, possibly leading to a blowout if the casing is allowed to become extremely worn. In a production well, deteriorated casing may permit undesirable "thiefing" of the flow to unwanted zones, thereby reducing the surface production. In an injection well, deteriorated casing may permit the injected fluid to flow to undesired formations.

Thus, it has been a long sought goal to provide accurate information concerning the condition of subsurface casing deterioration. In production wells, this information is useful when planning repairs and workovers or perforations of new intervals in already perforated casing. A related goal has been to make this information available as quickly and as effortlessly as possible.

A well known method of acquiring information regarding subsurface casing conditions, specifically the determination of the presence of defects in downhole casing strings, has been through the use of inspection instruments such as the one described in U.S. Pat. No. 3,543,144, issued to Walters et al on Nov. 20, 1970. The basic inspection instrument consists of an electromagnet, a magnetic sensing section, and two electronic packages to process the signals from the magnetic sensing section. During operation, a steady (DC) electromagnetic field of constant strength is generated by the inspection instrument. As the tool traverses the survey interval at a constant logging speed, the electromagnetic field permeates the casing wall with magnetic lines of flux. If there is no defect in the casing, the flux lines simply pass from one of the inspection instrument's poles, through the casing, and back to the other pole. If there is a defect in the casing wall, some of the electromagnetic field generated by the inspection instrument will "leak" out of the steel casing wall and flow around the defect. To detect such leakage, the inspection instrument includes two sets of contact shoes which survey the casing wall during a logging pass. Each shoe includes two Flux Leakage (FL) coils and two Eddy Current (EC) coils; one corresponding to each FL coil.

When an FL coil detects flux leakage (indicating a defect) the companion EC coil generates a signal if the defect is on the inside casing wall. No EC signal will be generated if the defect is on the outside casing wall. At the surface, a record is made of the greatest signal from each set of shoes. These record are commonly called FL-1, FL-2 and EC respectively. Lastly, all signals from one set of shoes are further processed to yield a fourth recorded signal FL AVE.

Of the four signals that can be recorded from this process, the two flux leakage signals, FL1 and FL2, are used to quantify the defect, or in other words, determine the percent of casing wall penetration in a defect. The third signal, EC, is used to qualify the defect to determine whether a defect is on the inside or outside of the casing wall. The fourth signal FL AVE is used to give an indication of the percent of the casing circumference that a defect occupies.

In order to interpret the information received from the inspection instrument and fully analyze the condition of the subsurface casing condition, considerable time and effort must be expended in the analysis of the recorded data. One problem that slows the interpretation of the data is that the structural configuration of the casing affects the existing data received from the inspection instrument. Each pipe collar, as well as hardware such as a centralizer, scratcher, or perforation, present along the casing length under inspection causes an undesirable response in the data received from the inspection instrument. These responses must be located and excluded from further analysis in order for the proper analysis of the state of casing deterioration to be made. To accomplish this analysis, visual inspection of the data provided by the inspection instrument and point-by-point comparison of the data recordings must be performed. Casing collars, centralizers, perforations and scratchers must be identified by the visual inspection of the responses of the received data and eliminated from the casing corrosion analysis.

Generally, data responses which have not been eliminated by the above described analysis are classified as defects. Once defects in the casing length have been identified, the corresponding point on the EC recording must be located in order to classify the defect as an inside defect (I.D.), i.e. located on the inside of the casing, or an outside defect (O.D.), i.e. located on the outside of the casing.

To determine the circumferential extent of a defect, i.e. how far around the casing the defect extends, the average response of the defect must be measured and compared to the typical average response at the collars. To determine the percent casing wall penetration for a defect requires the physical measurement of the FL response at that point followed by the graphical analysis of the data using the appropriate casing penetration chart.

While a detailed analysis of each of the casing defects is possible using the above procedure, an analysis of numerous casing defects quickly becomes exceedingly tedious. Furthermore, the task of an overall report on the general condition of casing with numerous defects becomes a difficult if not insurmountable job, requiring repeated defect analysis calculations like those described above, a comparison of the analyzed defects found throughout the entire casing length under investigation, followed by the highlighting of the most troublesome corrosion areas.

SUMMARY

An inspection instrument is passed through a length of casing to determine the extent to which corrosive deterioration of the casing length under inspection has occured. The inspection instrument generates four data measurements and delivers these data measurements to the surface facility for recording. Of these four data measurements, the first two (FL-1 and FL-2) are used to quantify any casing defect due to corrosion. The third measurement, EC, is used to qualify the defect, and the fourth measurement, FL AVE, is used to indicate the circumferential extent of that defect. Since the structural configuration of the casing length under inspection affects the data responses received from the inspection instrument, the data responses caused by defects in the casing due to corrosion and the data responses caused by the structural configuration of the casing must be separated.

The present invention analyzes the data from the inspection instrument and processes the data to exclude those data responses caused by the casing's structural configuration from any further analysis as defects caused by casing corrosion. The remaining data responses, which are considered indicators of casing defects caused by corrosion, are then processed to create a detailed analysis of the extent of corrosion present within the casing length under investigation. Among the information provided in this detailed analysis is the location and extent of the greatest defect in each casing joint, the circumferential extent of the greatest defect in each casing joint, and whether each of these defects is on the inside or the outside of the casing.

A feature of this invention is to provide a quantitative assessment of the degree of penetration of downhole corrosive damage and other casing defects. Another feature of this invention is to indicate whether the metal loss is internal or external. Still another feature of this invention is to indicate whether the metal loss is limited or general in circumferential extent. Yet another feature of this invention is to provide detailed information regarding downhole casing defects as quickly as possible. Still another feature of this invention is to measure the integrity of casing in storage or injection wells. Yet another feature of this invention is to establish the need for methods of preventing corrosion, as well as to determine the effectiveness of such methods after they are applied.

BRIEF DESCRIPTION OF THE DRAWINGS

The present invention may be better understood and its numerous objects and advantages will become apparent to those skilled in the art by reference to the accompanying drawings.

FIG. 1 is a generalized block diagram showing the path of the data under inspection in an embodiment of the method according to the invention for the evaluation of the state of deterioration of downhole casing.

FIG. 2 is a flowchart of the major steps of the method of processing the data logs received from the casing inspection instrument.

DESCRIPTION OF THE PREFERRED EMBODIMENT OF THE INVENTION

Figure 3:
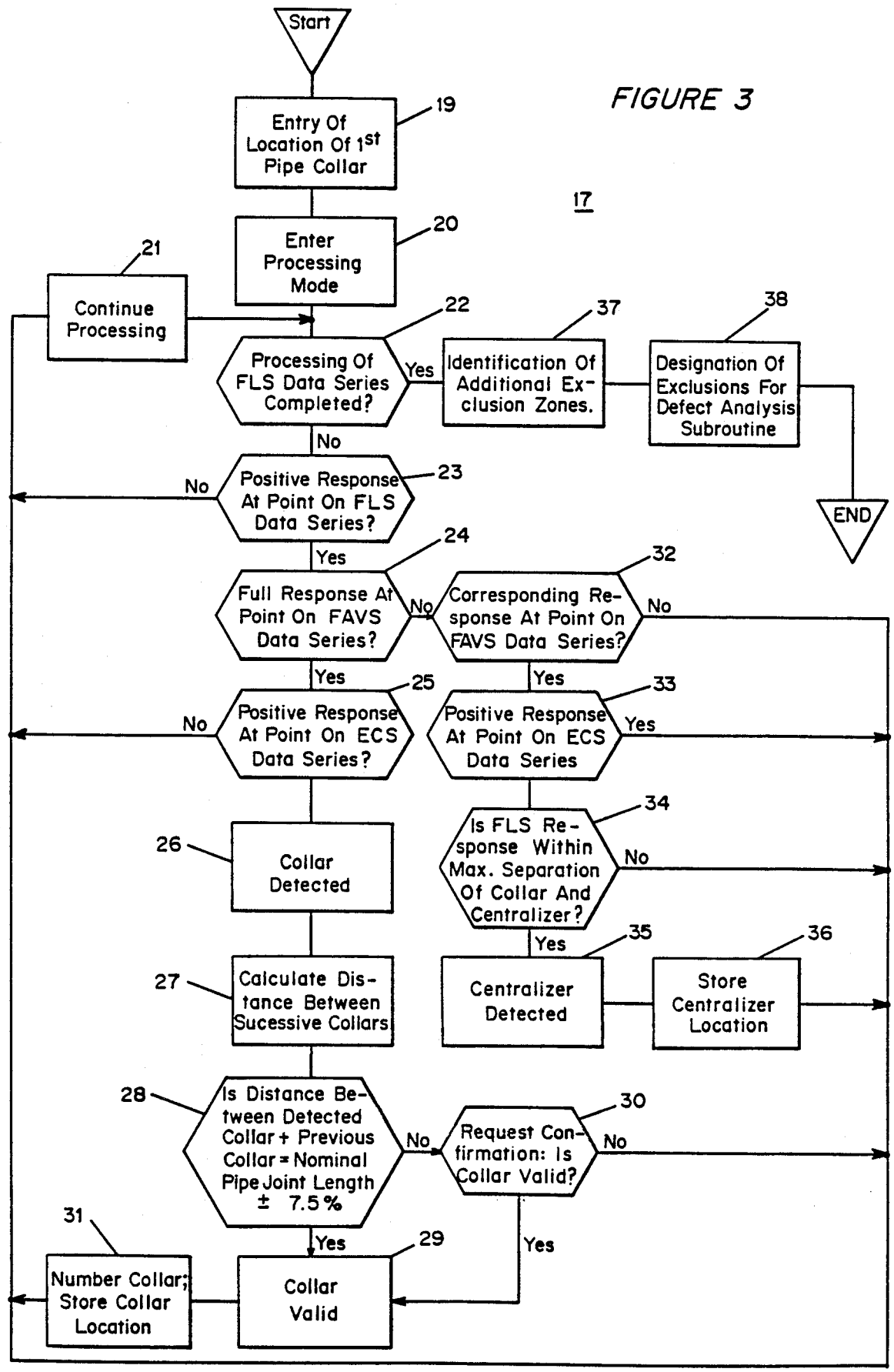
FIG. 3 is a more detailed flowchart of the data exclusion subroutine step of the flowchart of FIG. 2.

Referring to FIG. 1, within the inspection instrument 1 electromagnetic signals from the shoes 2 are processed by the FL electronics package 3 which generates the data series FL-1,6 and FL-2,7. The averaging electronics package 4 further processes the data series FL-1 to generate the data series FL AVE, 8. The EC electronics package 5 processes additional electromagnetic signals from the shoes 2 to generate the data series EC,9. After generation, the data series FL-1, FL-2, FL AVE, and EC are transmitted from the inspection instrument 1 via the wireline 10 to the surface recording system 11. After recording by the surface recording system 11, the data series FL-1, FL-2, FL AVE, and EC are transferred from the surface recording system 11 to the data processing system 12. The data processing system 12 interprets the recorded data series FL-1, FL-2 FL AVE, and EC and prepares a detailed analysis of the condition of the casing length under inspection for transmission from the data processing system 12 to the surface operator at 13. A more detailed description of the operation of inspection instrument 1 can be found in U.S. Pat. No. 3,543,144 which is incorporated herein by reference.

Referring to FIG. 2, the data processing system 12 of FIG. 1 is described in greater detail. The data series FL-1, FL-2, FL AVE, and EC are first subjected to depth shift correction 14. Depth shift is a delay in the receipt of data caused by the inspection instrument during the generation of the data series. The extent of the depth shift is readily determined and a correction factor designated. Data series FL-1 and FL-2 are then subjected to a comparator 15 which combines data series FL-1 and FL-2 into a single data series FL with duplicate signals removed. Data series FL, FL AVE and EC are then subjected to a noise reduction process 16 which compares the data series FL, FL AVE, and EC to a noise threshold value. If a point on the data series is determined to be less than the noise threshold value, that point is set equal to zero. Otherwise, the data point is left unchanged. The new data series resulting from the noise reduction process are FLS, FAVS and ECS. Data series FLS, FAVS and ECS are then subjected to the data exclusion subroutine 17 which edits FLS, FAVS and ECS to remove those responses which are caused by the structural configuration of the casing length under inspection. The edited data series FLS, FAVS and ECS are then subjected to a defect analysis subroutine 18 which performs a series of manipulations of the received data while preparing a detailed analysis of the condition of the casing length under inspection.

Referring to FIG. 3, a detailed block diagram of the data exclusion subroutine 17 is shown. The subroutine is first synchronized to the location of the first pipe collar at 19. The subroutine enters the processing mode at 20. In the processing mode, the FLS data series is searched for responses. The subroutine will exit the processing mode at 22 when the subroutine detects that the entire FLS data series has been processed. The subroutine searches a point on the FLS data series for a response at 23. If no FLS response is detected at 23, then the subroutine will continue processing the sucessive point of the FLS data series at 21. If an FLS response is detected at 23, then the corresponding point of the FAVS data series will be examined at 24. If the response of the FAVS data series at the corresponding point is considered a full response (A "full" response being defined as a response with magnitude approximately equivalent to the magnitude of the response at the first pipe collar), then the corresponding point of the ECS data series will be examined at 25. If an ECS response is detected at 25, then the subroutine will declare a detected collar at 26. If no ECS response is detected at 25, then the subroutine will return to 21 to continue processing the succesive point of the FLS data series. If the subroutine declares a detected collar at 26, then the distance between the detected collar and the previous collar will be calculated at 27. If the distance between the detected collar and the previous collar is found at 28 to be within 7.5% of the present nominal pipe joint length, then the collar is declared valid at 29. If the distance between the detected collar and the previous collar varies from the nominal pipe joint length by more than 7.5%, then confirmation of the collar will be requested at 30. If the collar is confirmed at 30 then the collar will be declared valid at 29. If no confirmation of the detected collar is made at 30, then the subroutine will return to 21 for processing of the successive point of the FLS data series. If the subroutine has declared a valid collar at 29, then the collar will be numbered and its location stored at 31. The length of casing between two such collars is termed a casing joint. The subroutine will then return to 21 for processing of the successive point of the FLS data series.

Returning to step 24 of the subroutine, if the response of the FAVS data point is not considered a full response, then the FAVS response will be compared at 32 to a corresponding response for a centralizer (A corresponding response is generally considered a response of substantial magnitude but which is of noticeable less magnitude than a "full" response). If there is no corresponding FAVS response at 32, then the subroutine will return to 21 for processing of the successive point of the FLS data series. If a corresponding FAVS response is detected at 32, then the corresponding point of the ECS data series will be examined at 33. If there is an ECS response at 33, then the subroutine will return to 21 for processing of the successive point of the FLS data series. If there is no ECS response detected at 33, then the subroutine will determine at 34 whether the FLS response is within the entered maximum separation between a collar and a centralizer. If the FLS response is within the maximum separation between a collar and a centralizer, then the subroutine declares a detected centralizer at 35, stores the centralizer location at 36, and return to 21 for further processing. If the FLS response is not within the maximum separation, then no centralizer is declared and the subroutine will return to 21 for further processing.

Upon completion of processing of the FLS data series at 22, the subroutine will then permit identification at 37 of additional FLS data to be excluded from the defect analysis subroutine 18. The subroutine then designates at 38 all centralizers, collars, and other designated portions of the FLS data series as exclusion zones. Any FLS responses within the exclusion zones will not be considered as possible defects during the defect analysis subroutine 18.

Figure 4:
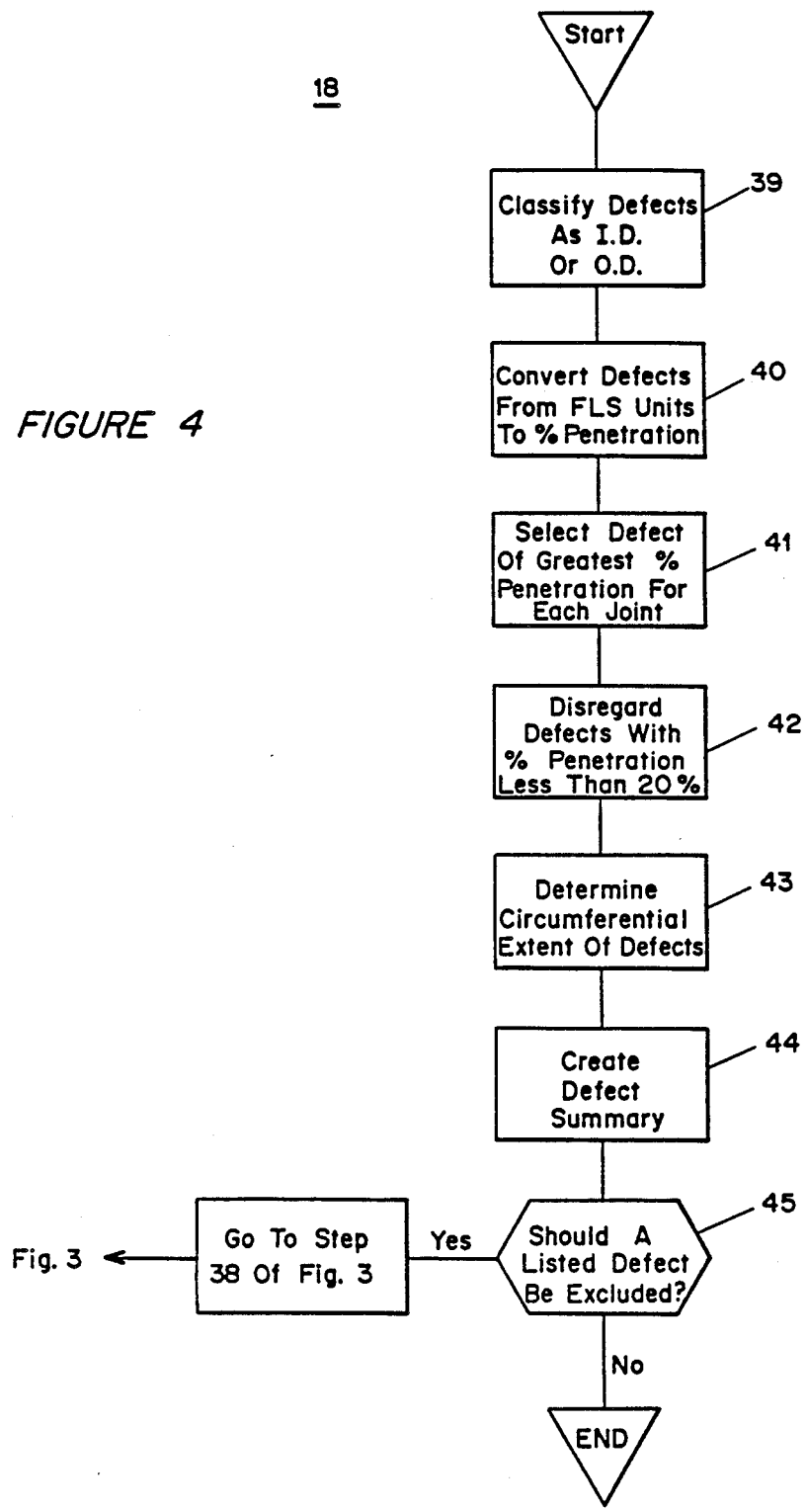
FIG. 4 is a more detailed flowchart of the defect analysis subroutine step of the flowchart of FIG. 2.

Referring to FIG. 4, a detailed block diagram of the defect analysis subroutine 18 is shown. All remaining positive FLS log responses that were not eliminated by the data exclusion subroutine 17 are considered possible defects. The defect analysis subroutine first determines whether each possible defect is an inside defect or outside defect at 39 by examining the corresponding ECS response for each possible defect. The subroutine will designate each possible defect as an inside defect (I.D.) if there is an ECS response or as an outside defect (O.D.) if there is no ECS response. The defects will be converted at 40 from FLS units to the corresponding percent penetration through the use of conversion charts stored internally. Choice of which of the stored conversion charts is to be used to convert the defect penetration from FLS units to percent penetration is made with the use of the methods disclosed in the application with Ser. No. 946,150 continuation of application No. 799,255, abandoned.

Preceeding to step 41, the subroutine then selects from the defects the defect of greatest magnitude in percent penetration between each successive collar. The defects of greatest magnitude between successive collars which have a percent penetration less than a specified value, such as 20%, are eliminated at 42 from further consideration. For each of the remaining defects of greatest magnitude between successive collars, the circumferential extent of the defect is calculated at 43 by dividing the FAVS response at each defect by the FAVS response at a collar. A defect summary comprising of the location and physical characteristics of the maximum defect with penetration greater than 20% located between sucessive collars of the casing length is created at 44. Any of the listed defects may then be edited out at 45. Should a listed defect be edited out, the data processing system 12 will exit the defect analysis subroutine 18 and re-enter the data exclusion subroutine 17 at step 38 of FIG. 3. An additional exclusion zone for the listed defect to be edited out will be designated at 38. The data exclusion subroutine 17 will then be exited and the defect analysis subroutine 18 will be restarted with the expanded FLS data series exclusion zones being used. Returning to step 45, once all listed defects are satisfactory, the defect analysis subroutine 18 will be completed.

The embodiments of the invention in which an exclusive property or privilege is claimed are defined as follows:

1. A method of evaluating state of deterioration due to corrosion of a string of subsurface well casing having a plurality of tubular casing lengths by passing an inspection instrument through the inside of a casing length under inspection and submitting signal outputs of said inspection instrument to a process of analysis to exclude effects of structural configuration about said casing comprising the steps of:
   deriving first and second measurements from said inspection instrument;
   combining said first and second measurements;
   analyzing said combined measurement and excluding responses caused by said structural configuration about said casing therefrom wherein the step of analyzing said combined measurement and excluding responses caused by said structural configuration about said casing therefrom further comprises the steps of:
      locating collars along said casing length under inspection; and
      excluding from analysis for evaluating said state of deterioration responses caused by said collars; and
      analyzing remaining response for evaluating said state of deterioration of said casing;
   deriving a third measurement from said inspection instruments; and
   comparing said third measurement to said combined measurement to determine whether casing defects are located inside or outside of the said casing.

2. The method of claim 1 further comprising the additional step of manipulating said combination measurement to determine percent of casing wall penetration for said casing defects.

3. The method of claim 2 further comprising the additional steps of:
   deriving a fourth measurement from said inspection instrument; and
   comparing responses from said fourth measurement caused by said casing defects to responses from said fourth measurement caused by said structural configuration about said casing to determine circumferential extent of said casing defects.

4. The method of claim 3 wherein the step of analyzing said remaining responses for evaluating said state of deterioration of said casing comprises the steps of:
   classifying each of said remaining responses of said combined measurement as a defect in said casing located inside of said casing length or outside of said casing length;

converting said defect in said casing to percent penetration;

selecting a defect in said casing of maximum penetration for each of said casing lengths;

determining circumferential extent of said maximum defect for each of said casing lengths; and generating a summary of the status of said maximum defect for each of said casing lengths.

5. A method of evaluating state of deterioration due to corrosion of a string of subsurface well casing having a plurality of tubular casing lengths by passing an inspection instrument through the inside of a casing length under inspection and submitting signal outputs of said inspection instrument to a process of analysis to exclude effects of structural configuration about said casing comprising the steps of:

deriving first and second measurements from said inspection instrument;

combining said first and second measurements;

analyzing said combined measurement and excluding responses caused by said structural configuration about said casing therefrom wherein the step of analyzing said combined measurement and excluding responses caused by said structural configuration about said casing therefrom further comprises the steps of:

locating collars along said casing length under inspection;

locating centralizers along said casing length under inspection; and excluding from analysis for evaluating said state of deterioration responses caused by said collars and said centralizers; and analyzing remaining response for evaluating said state of deterioration of said casing;

deriving a third measurement from said inspection instruments, and comparing said third measurement to said combined measurement to determine whether casing defects are located inside or outside of said casing.

6. The method of claim 5 further comprising the additional step of manipulating said combined measurement to determine percent of casing wall penetration for said casing defects.

7. The method of claim 6 further comprising the additional steps of:

deriving a fourth measurement from said inspection instrument; and comparing responses from said fourth measurement caused by said casing defects to responses from said fourth measurement caused by said structural configuration about said casing to determine circumferential extent of said casing defects.

8. The method of claim 7 further comprising the additional steps of:

editing at said maximum defect for a casing length in response to a command;

excluding additional responses of said combined measurement in response to said editing;

classifying each of said remaining responses of said combined measurement as a casing defect inside of said casing length or outside of said casing length;

converting said casing defects to percent penetration;

selecting said defect of maximum penetration for each of said casing lengths;

determining circumferential extent of said maximum defect for each of said casing lengths; and generating a summary of the status of said maximum defect for each of said casing lengths.

* * * * *